United States Patent
Anthony et al.

(10) Patent No.: US 7,497,330 B2
(45) Date of Patent: Mar. 3, 2009

(54) APPARATUS FOR SHARP IMPLEMENT TRANSFER, COUNTING AND TEMPORARY DISPOSAL OR STORAGE

(75) Inventors: Robert Anthony, Akron, OH (US); Daniel P Guyton, Akron, OH (US); Douglas M. Evans, Akron, OH (US); John R. Hickman, Tallmadge, OH (US)

(73) Assignee: Neutral Field, LLC, Akron, OH (US)

( * ) Notice: Subject to any disclaimer, the term of this patent is extended or adjusted under 35 U.S.C. 154(b) by 304 days.

(21) Appl. No.: 11/360,063

(22) Filed: Feb. 23, 2006

(65) Prior Publication Data

US 2006/0138004 A1 Jun. 29, 2006

Related U.S. Application Data

(63) Continuation of application No. 10/634,072, filed on Aug. 4, 2003, now Pat. No. 7,036,661, which is a continuation-in-part of application No. 09/847,969, filed on May 2, 2001, now abandoned.

(60) Provisional application No. 60/203,363, filed on May 10, 2000.

(51) Int. Cl.
*B65D 83/10* (2006.01)
*A61B 17/06* (2006.01)

(52) U.S. Cl. .................... 206/363; 206/438

(58) Field of Classification Search .............. 206/210, 206/363, 365, 366, 818; 211/DIG. 1; 128/846, 128/877, 878
See application file for complete search history.

(56) References Cited

U.S. PATENT DOCUMENTS

| | | | |
|---|---|---|---|
| 1,867,738 A | 7/1932 | Fraser | 206/815 |
| 1,933,894 A | 11/1933 | Clink | 206/234 |
| 2,589,349 A | 3/1952 | Diefenbach | 131/241 |
| 2,941,691 A | 6/1960 | Weinberg | 220/345.2 |
| 3,610,459 A | 10/1971 | Hanson | 206/818 |
| 3,756,387 A | 9/1973 | Chaney | 206/3 |
| 3,899,073 A | 8/1975 | Barr | 206/815 |
| 4,113,098 A | 9/1978 | Howard | 206/540 |
| 4,303,158 A | 12/1981 | Perkins | 206/373 |
| 4,513,974 A * | 4/1985 | Lin | 273/239 |
| 4,643,303 A | 2/1987 | Arp et al. | |
| 4,694,950 A | 9/1987 | Macleod, Jr. | 198/465.3 |
| 5,024,326 A * | 6/1991 | Sandel et al. | 206/366 |
| 5,044,500 A | 9/1991 | Webber et al. | 206/456 |
| 5,363,862 A * | 11/1994 | Mercier | 128/846 |
| 5,388,691 A | 2/1995 | White | 206/305 |
| 5,405,004 A | 4/1995 | Vest et al. | 206/350 |
| 5,492,671 A | 2/1996 | Krafft | |
| 5,577,629 A | 11/1996 | Rosler | 220/345.3 |

(Continued)

*Primary Examiner*—Mickey Yu
*Assistant Examiner*—Melissa L Lalli
(74) *Attorney, Agent, or Firm*—Pearne & Gordon LLP

(57) ABSTRACT

The invention relates to a multipurpose device for the safe handling of sharp surgical implements and comprises a molded thermoplastic body that includes a container portion and a scalpel holder section. Magnetic material in the container holds scalpel blades and/or needles after use and magnetic material on the holder section presents a needle for pick-up by a needle holder. The scalpel holder section supports a scalpel or scalpels in cantilever fashion for convenient gripping and withdrawal by a surgeon. The body has a shape and surface characteristics that assures a secure hand grip even in wet conditions.

13 Claims, 6 Drawing Sheets

U.S. PATENT DOCUMENTS

| | | | |
|---|---|---|---|
| 5,609,252 A | 3/1997 | Koch | 206/449 |
| 5,620,109 A | 4/1997 | Madden | 220/345.4 |
| 5,894,925 A * | 4/1999 | Sukiennik et al. | 206/356 |
| 5,911,320 A | 6/1999 | Forestelle | 206/215 |
| 6,119,862 A | 9/2000 | Childress | 206/557 |
| 6,210,638 B1 | 4/2001 | Grieco et al. | 220/345.1 |
| 6,244,447 B1 | 6/2001 | Frieze et al. | |
| 6,391,260 B1 | 5/2002 | Davis | 422/28 |
| 7,159,714 B2 * | 1/2007 | Wilkinson et al. | 206/366 |

* cited by examiner

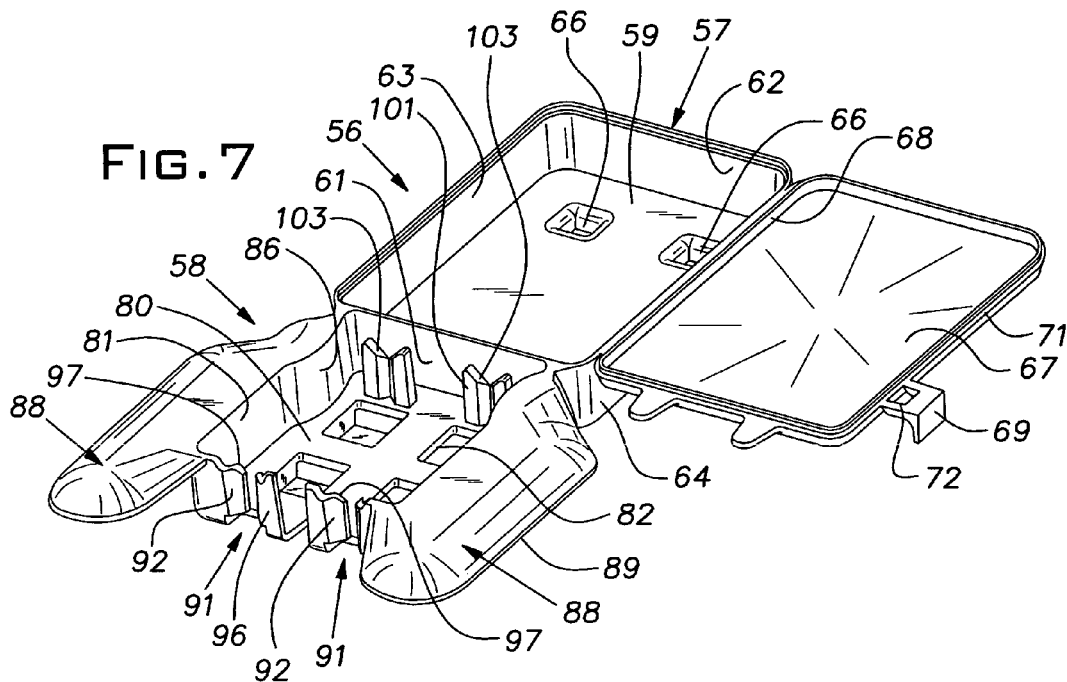

APPARATUS FOR SHARP IMPLEMENT TRANSFER, COUNTING AND TEMPORARY DISPOSAL OR STORAGE

This application is a continuation of application Ser. No. 10/634,072, filed Aug. 4, 2003 now U.S. Pat. No. 7,036,661, which application is a continuation-in-part of application Ser. No. 09/847,969, filed May 2, 2001 now abandoned, which application claims the priority of U.S. Provisional Application No. 60/203,363, filed May 10, 2000.

TECHNICAL FIELD

The invention relates to an improved design for a container which is a health care safety product designed to help protect against accidental injury during the passage of sharp instruments; i.e., suture needles and scalpels within the performance of any surgical procedure. It does not involve direct patient contact.

BACKGROUND OF THE INVENTION

There are approximately 500,000 to 800,000 needle stick injuries reported each year regarding healthcare professionals in the United States. Other than in the patient's room, these accidents occur most often in the operating room. As a result of this significant health hazard, health device manufacturers have developed various products designed to protect healthcare professionals. These items include retractable syringes, "sharps" containers, syringe covers, syringe guards, etc. While needle sticks associated with syringes account for an estimated 75% of the problem, it is estimated that most of the remaining 25% are the result of sticks associated with suturing during surgical procedures or during the unprotected passing of these sharps. It is this niche which has not been adequately adressed by suture manufacturers who have left it up to the discretion of the end user to provide their own protection.

The Occupational Safety & Health Administration (OSHA) in directive #CPL2-2.44D, issued Nov. 5, 1999 mandated a change in the Federal Blood Borne Pathogens Act. They called for a shift in work practice controls and issued a call for engineering solutions for use when sharps are passed from one individual to another. The Act states, "The employer must use engineering and work practice controls to eliminate occupational exposure or reduce it to the lowest feasible extent." Further, they specifically called for the elimination of "hand-to-hand" or direct passing of all sharps. The overall goal is to reduce the risk of accidental needle or scalpel injuries during this process.

Additionally, they issued four engineering design requirements which include:

(1) A thick safety feature that provides a barrier between the hands and needle after use. The safety feature should allow or require the worker's hands to remain behind the needle at all times;

(2) The safety feature is an integral part of the device and not an accessory;

(3) The safety feature is in effect before disassembly and remains in effect after disposal to protect users and trash handlers; and (4) The safety feature is as simple as possible, requiring little or no training to use effectively.

The apparatus of the present invention is designed to meet all of OSHA's design requirements while remaining user friendly and without the incorporation of new hand movements during an operation. It is compact, hand-held, and functions for both suture needles of all sizes as well as scalpels. Additionally, it functions as a safe return device (i.e., passing of sharps occurs in two directions). Moreover, it acts as a counting device for needles and also functions as a temporary storage and/or disposable container for used suture needles and scalpels. Known efforts to date have been focused on prevention of syringe needle sticks with retractable syringes. Simple guard type devices are also available for some scalpels. No other multi-functional yet simple device for use with suture needles and scalpels that also satisfies the new OSHA requirements is known.

The Prior Art fails to recognize the value in coupling slots for use with sharp implements which effectively immobilize the sharp implement for transfer purposes, coupled with a magnetically enhanced disposal compartment for easy counting and disposal. By using the novel design of the present invention, coupled with the new system arrangement of the essential elements of the invention, a more flexible configuration is shown which overcomes the inherent limitations of the teachings of the Prior Art as well as permitting a wider range of applications, not permitted with the presently available systems.

SUMMARY OF THE INVENTION

The invention eliminates many of the inherent limitations of the Prior Art by designing an apparatus which, in one embodiment, is composed of a rectangular box of clear plastic with approximately half of the box top open. Magnets are embedded within to secure the needle mounted in a special slot. A sliding door on the top half holds sharps (i.e. used suture needles and scalpel blades). The scalpel anchors are similarly embedded and designed to cover the scalpel itself while exposing only the handle. In this preferred embodiment, it is designed for single use, although reusable versions are contemplated.

It is an object of this invention to provide an apparatus which is designed to meet all of OSHA's new regulations, be hand-held and compact, with dual functions for both suture needles as well as scalpels.

These and other objects of this invention will be evident when viewed in light of the drawings, detailed description, and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein:

FIG. 7 is a perspective view of the main body of a second version of a sharp instrument handling device shown with its cover open;

FIG. 8 is a perspective view of a bottom side of the device of FIG. 7;

DETAILED DESCRIPTION OF THE INVENTION

Figure 1:
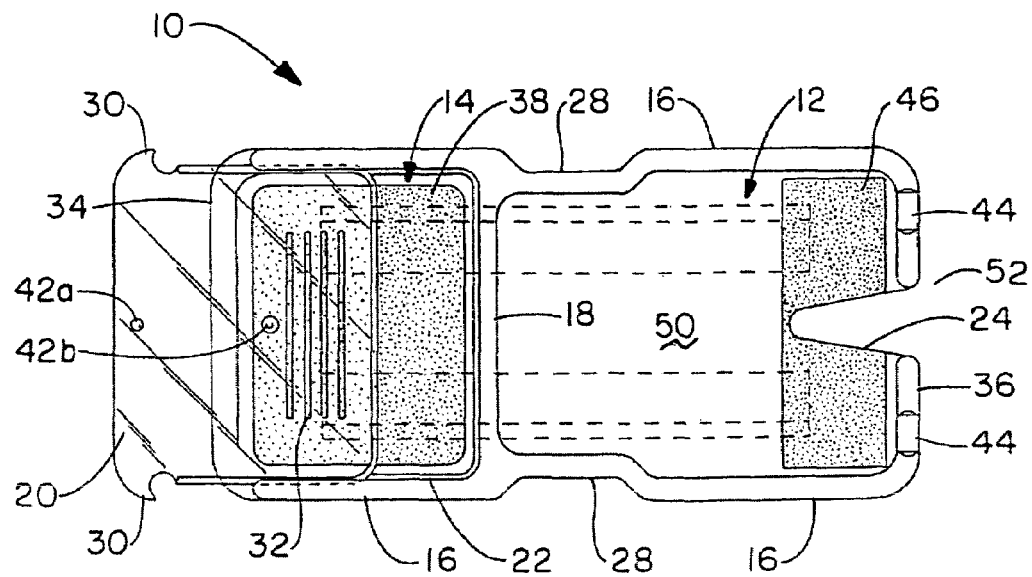
FIG. 1 is a top view of the apparatus comprising this invention showing a sliding door in a partially open position.

Referring now to the drawings wherein the showings are for purposes of illustrating the preferred embodiment of the invention only and not for purposes of limiting the same, the Figures show the apparatus for sharp implement transfer, counting and temporary disposal or storage of the present invention.

This device is hand-held and at least partially constructed of clear plastic with embedded magnets. The chosen material of construction must be capable of withstanding a sterilization environment, although in one embodiment, it will only be used once. Traditionally, suture needles, scalpels and other sharps are passed "hand-to-hand" or directly from assistant to surgeon. As an example, in the course of an operation, the passing of sharps occurs in the following steps. The assistant removes the needle from the sterile package and mounts the needle on a needle holder. The needle is exposed. The assistant then "passes" the needle and holder to the surgeon using direct, hand-to-hand technique. The surgeon, when completed, then passes the needle back to the assistant. Again, the needle/scalpel remains exposed at all times during this process.

The needle escort provides protection during each step of the above procedures. First, the assistant uses a needle holder to mount the needle within the protective escort device. Secondly, the needle escort device is passed with the hands behind the needle, as specified in OSHA requirements. The only way for the surgeon to access the needle is with a needle holder, not with the use of hands or fingers. When complete, the surgeon disposes the needle in the top retractably sealable box where the used needle remains until the end of the case, at which time all needles are easily counted and the entire device is properly disposed of, in a permanent fashion, in an appropriate permanent sharps disposal container. The needle escort is unique in that it incorporates protection without being cumbersome. It is lightweight and disposable. It is designed for both forward and backward passing of instruments and eliminates direct hand-to-hand passing and exposure during the above process.

Figure 2:
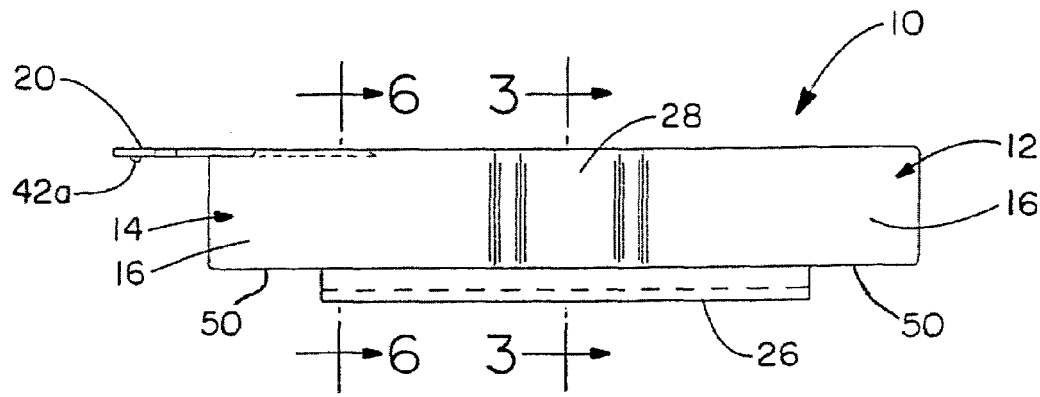
FIG. 2 is a side elevational view of the apparatus shown in FIG. 1.

As seen in FIGS. 1 and 2, the apparatus 10 comprises a two-compartment system in which sterilized sharp implements are removably positionable for suturing use in exposed holding and handling receptacle 12 and sharp implements for either storage or subsequent disposal are placed in sealable disposal and storage compartment 14. The apparatus has a pair of longitudinal side walls 16, a pair of end walls 34,36, a floor 50, and in a preferred embodiment, an inner wall 18 which separates the holding and handling receptacle 12 from the disposal and storage compartment 14.

Figure 3:
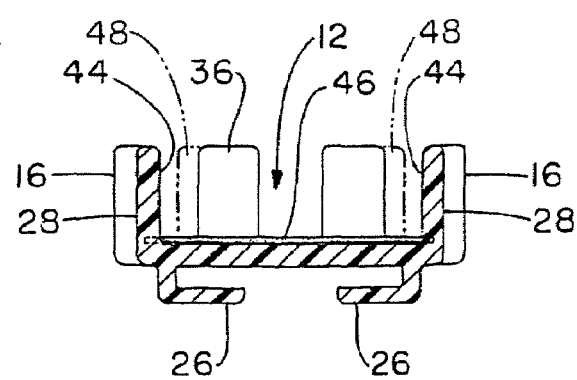
FIG. 3 is a cross-sectional view as may be taken at the line 3-3 in FIG; 2.

As illustrated in FIGS. 1 and 3, the holding and handling receptacle 12 comprises a pair of longitudinal side walls 16, floor 50, inner wall 18, which in a preferred embodiment is shared with adjacent disposal and storage compartment 14, and exterior receptacle end wall 36. In one embodiment of the invention end wall 36 is discontinuous at three locations, although this number could be increased or decreased, and optionally, eliminated. As evidenced in FIG. 1, a pair of slots 44 are shown in spaced apart relationship to each other and positioned toward longitudinal side walls 16. These openings are available for scalpel insertion and holding when passed from a physician's assistant to a physician. In a preferred embodiment, a third opening 52 is present which in cooperation with V-shaped notch 24 in floor 50 facilitates linkage with suture material, i.e., thread which is held in engagement with the apparatus 10 through suture card (not shown) which is secured via opposed rails 26.

Figure 6:
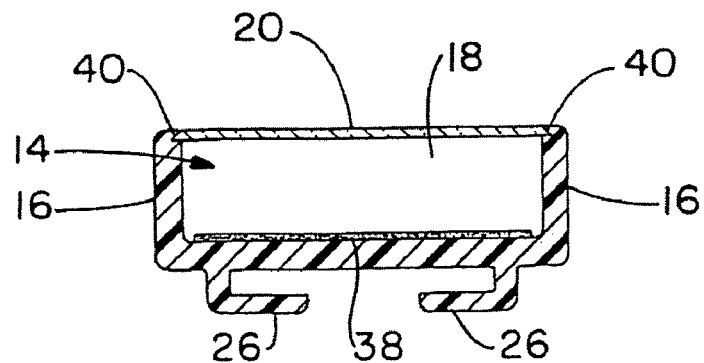
FIG. 6 is a cross-sectional view taken at the line 6-6 in FIG. 2 and showing an alternative configuration for a wall which divides the two compartments of the apparatus.

As illustrated in FIGS. 1 and 6, the sealable disposal and storage compartment 14 comprises a pair of longitudinal side walls 16, a floor 50, an inner wall 18, which in a preferred embodiment is shared with adjacent holding and handling receptacle 12, and exterior compartment end wall 34. The end wall is slightly lowered in comparison to side walls 16 to accommodate sliding engagement of a securely fastenable covering device 20, which for safety purposes, prevents the sharp implement from falling out of the apparatus when it is positioned in a manner other than laying flat on a horizontal surface. In a preferred embodiment, this covering device 20 will be slidably positionable via grooves 22 inside exterior walls 16 of disposal and storage compartment 14 and commonly shared interior wall 18. The longitudinal side walls 16 preferably have an indentation 28 contained at approximately the mid-point along the length to accommodate holding the apparatus between a thumb and a finger of a user.

Figure 4:
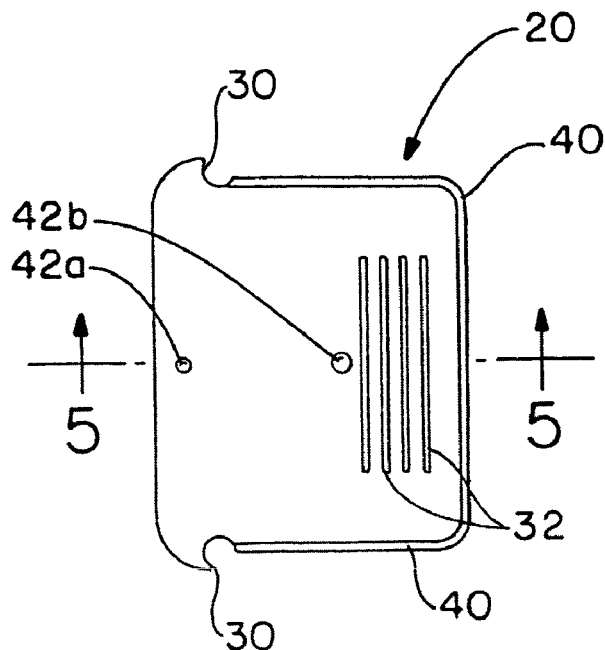
FIG. 4 is a top view of the sliding door.
Figure 5:
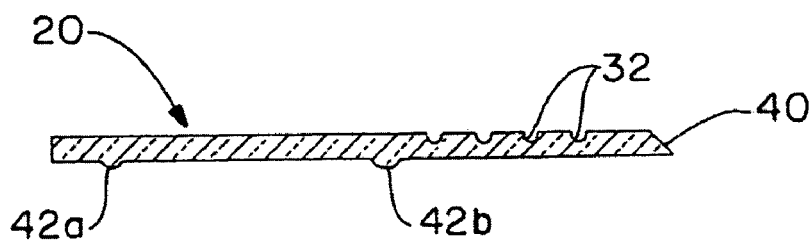
FIG. 5 is an enlarged cross-sectional view of the door shown in FIG. 4 as taken at the line 5-5 thereof.

In order to securely position the sharp implements and/or needles, a pair of magnets 46 are securely positioned on floor 50 adjacent end wall 36 of holding and handling receptacle 12. For disposal, at least one magnet 38 is positioned in disposal and storage compartment 14 for securing the sharp implements prior to closing of the receptacle by cover member 20. Optionally, as best illustrated in FIG. 4, the covering device will have a pair of laterally extending hooks 30 for stop positioning of the cover member 20 against longitudinal side walls 16 and a protruding lip 40 along two longitudinal sides and one interior side of the cover member for insertion into grooves 22 on the interior of longitudinal side walls 16 of disposal and holding compartment 14. For ease of movement, a plurality of grooves 32 are either molded as raised edges or cut into cover member 20. In a preferred embodiment, a first raised ridge 42a as best seen in FIG. 5, is molded into cover member 20 on the under side for ensuring secure engagement with an interior side of lowered end wall 34 of the disposal and holding compartment 14 of cover member 20. Additionally, a second raised ridge 42b is shown positioned interiorly of first raised ridge 42a to minimize the possibility of cover member 20 falling to the floor upon lateral peripheral movement by a user effected to opening the cover member.

As seen in FIG. 3, a pair of openings 44 in exterior receptacle end wall 36 permit insertion of scalpel blades with associated grooved handles, said handle grooves typically being normal to the longitudinal axis of the scalpel and dimensioned so as to frictionally fit into openings 44 in end wall 36. In one embodiment of this invention, foam or flexible inserts 48 are positioned within opening 44 so as to accommodate differently sized scalpel handles.

When the device is being used in association with suture materials (not shown), typically provided in sterile elongated packaging dimensioned so as to be frictionally positionable within inwardly directed legs 26 after removal of the packing material, the sterilized needle with suture material threadably attached, is positioned using a needle holder onto magnets 46 with suture material passing through notch 24 in floor 50. After the threaded needle has been positioned onto magnets 46, the needle holder is disengaged from the needle and apparatus 10 held in a forward facing position exposed to the physician or suture technician. After passing, the needle is reattached to the needle holder for use by the physician or suture technician to effect the closure. Upon completion of the closure, the needle is deposited onto magnet 38 in the disposal and holding compartment 14 after opening of securely refastenable lid 20, followed by disengagement of the needle holder and closure of lid 20.

While securely refastenable lid 20 has been described so far as a slidably repositionable device with a ridge which is guided by a groove in the disposal and holding compartment 14, there is no need to limit it to such. One of the key considerations is the degree of integrity of the closure coupled with the magnet which is positioned along at least a portion of the bottom of the compartment. Alternative lid configurations could include, a hinged arrangement with frictional snap fit characteristics. Yet further embodiments, include encasing the magnet into either the floor of the compartments or in separable plastic inserts dimensioned so as to be positionable within either one or both of the compartments. This is anticipated to be helpful when the device is intended for multiple uses, and sterilized multiple times.

In light of the sterilization requirement, it is important that any plastic which is employed to manufacture the apparatus be capable of withstanding sterilization environments. Typical of sterilizable polymers would include the following non-limiting examples: poly(meth)acrylics, e.g., poly(meth)acrylic acids and esters thereof, e.g., poly(meth)acrylates, polyamides such as nylon, polyesters and polyolefins such as polyethylene, including ultra high molecular weight polyethylene and crosslinked polyethylenes or polypropylene, polyetherimides, acetal copolymers, polyethersulfones, polyarylethersulfones, polysulfones, PPO (polyphenylene oxide & styrene), polystyrenes, polycarbonates, and ABS (acrylonitrile butadiene styrene).

In order to implement the OSHA directives, it is important that cover member 20 be transparent or translucent so as to enable counting of the sharps contained within disposal and holding compartment 14. Other structural members of the apparatus need not have either the transparent or translucent characteristic.

Figure 11:
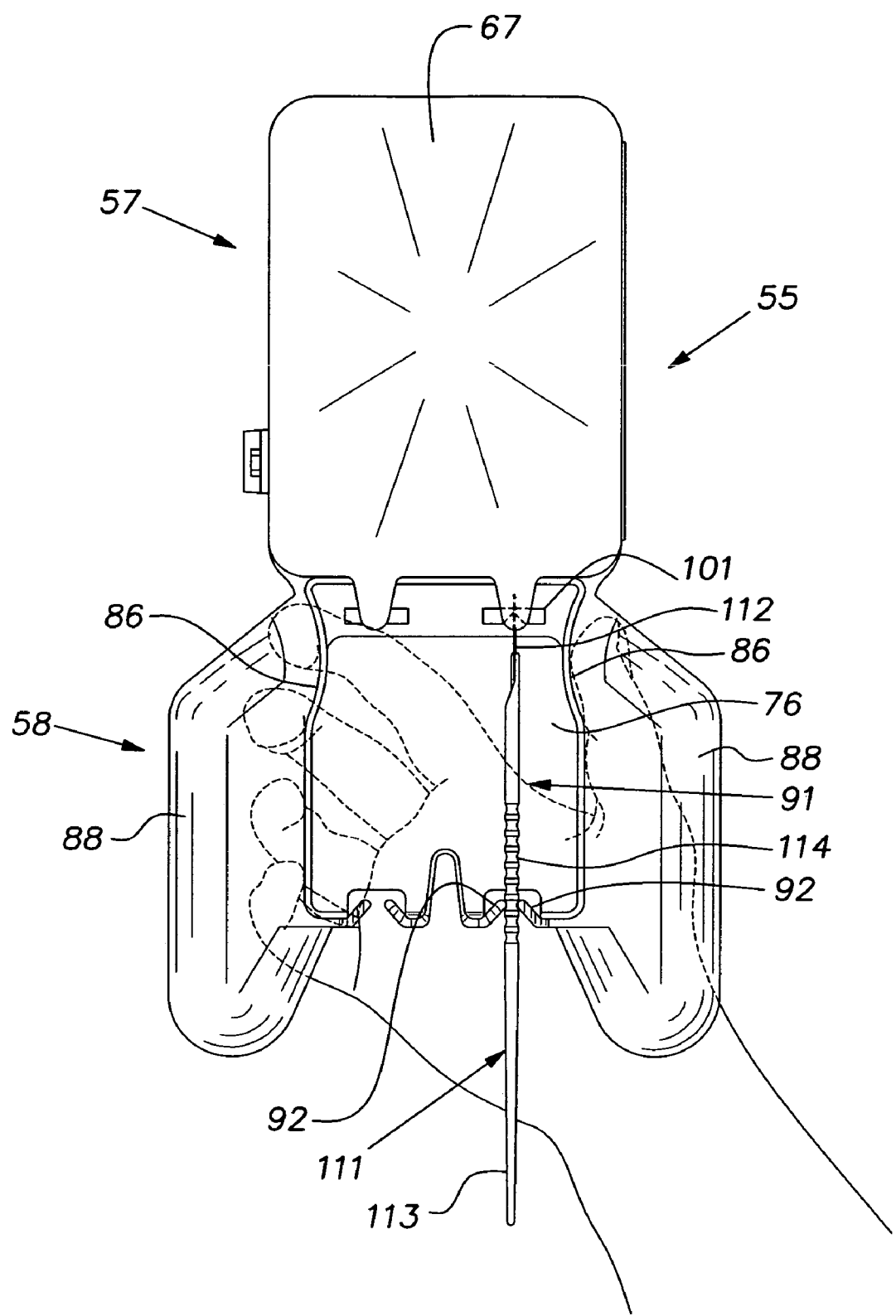
FIG. 11 is a perspective view of the device of FIG. 7 in a hand-held orientation and carrying a scalpel for presentation to a surgeon.

FIGS. 7-12 illustrate another version of a sharp surgical instrument handling device 55 constructed in accordance with the invention. The main part of the device 55 comprises a one-piece or unitary injection molded body 56. The body 56 is formed of a suitable thermoplastic such as polypropylene with various thin wall portions having, for the most part, a generally uniform thickness. The body 56 has two principal sections, a box-like container section 57 and a specialized implement support section 58. The illustrated device 55 has an overall length (FIG. 10) of about 7⅝". Ideally, the corners of various parts of the body are rounded to avoid cutting or tearing of gloves worn by medical personnel. The box section 57 is generally rectangular in plan view (FIG. 9) and is relatively shallow by virtue of having a depth of about ⅕ its major length measured in the longitudinal direction of the device 55, that is, the lengthwise direction of the body 56. The box section 57 includes a bottom wall 59, end walls 61, 62, and sidewalls 63, 64. The bottom wall 59, at an area remote from the support section 58, includes a pair of molded-in supports or feet 66 that depend downward from the bottom wall proper. A lid or cover 67 is joined to one of the side walls 64 with a living hinge 68. The lid 67 is molded in the open position of FIG. 7 and can be closed over the container 57 as indicated in FIG. 11. The cover 67 is large enough to fully close the container 57 and is releasably locked in a closed position by a resiliently deflectable latch formed on a free edge 71 of the cover 67. A hole 72 in the latch 69 receives a small projection 73 on a sidewall 63 (FIG. 8).

A magnetic sheet 76 (FIGS. 9, 11) is assembled on the bottom wall 59 on the inside of the container or box 57 by suitable adhesive or other means. Printed or otherwise marked on the exposed side of the magnetic sheet 76 is a rectangular grid of a color contrasting with the sheet that is used to count or register sharp implements such as used scalpel blades and needles by receiving a separate one of the implements in a single one of the grid spaces. The cover 67 is preferably sufficiently transparent to enable the grid and any sharps on the magnetic sheet 76 to be seen therethrough.

The implement support section 58 has a base wall 80 that, as shown, can be coplanar with the bottom wall 59 of the box section 57. Opposed vertical walls 81 reinforce the base wall 80 by interconnecting it with the container box section end wall 61. The base wall 80 has square or rectangular apertures 82 that simplify the tooling required to mold a plurality of right angle tabs 83. The tabs 83 serve as support feet for the device 55 and to resiliently grip a suture pack as described below. The bottom surfaces of the tabs 83 and feet 66 are preferably coplanar and are provided with double-side adhesive-coated foam-like pads 84 of known construction. The lower surfaces of the pads 84, ideally, have peel-away release liner material which, when removed, enables the device 55 to be adhered to a supporting surface such as a surgical drape or table. The sidewalls 81 are formed with concave areas 86 that cooperate to create a wasp waist configuration adjacent the container box 57 so as to produce a comfortable and secure finger grip across these areas 86 (FIG. 11).

Finger guards 88 extend laterally from upper edges of the walls 81 and longitudinally beyond the forward end of these walls and the base wall 80. The finger guards 88 are cupped downwardly along the majority of the length of their free edges 89 towards the bottom face of the device, i.e. they are concave from the lower face of the device 55. The free edges 89 of the finger guards remain above the plane of the bottom wall 59 and coplanar base wall 80 so as to not interfere with the function of the feet 66 and tabs 83 for supporting the device 55 in a stable manner on a flat surface.

At a forward end of the base wall 80 are two scalpel holding locations 91 each formed by a pair of opposed gripping elements in the form of upstanding or vertical tabs 92. The tabs 92 lie in planes oblique to the longitudinal direction of the device 55 so that the tabs in a free state converge towards one another with reference to the rearward direction. Edges 93 of the pair tabs in a free state are spaced from one another to define a gap 94. The central tabs 92 are supported on fingers 96 having vertical and horizontal segments. At their upper ends, the tabs 92 are formed with inclined camming edges 97 such that the gap 94 between the tab edges widens with increasing distance from the base wall 80. A space or notch 98 exists between the fingers 96 and extends a limited distance into the base wall 80.

An upstanding or vertical rib 101 near the box 57 is aligned in the longitudinal direction with each gap 94. As indicated, each rib 101 is formed with a lengthwise deep groove 102 dividing the rib into two portions and leaving only a very thin membrane 100 of material between these portions adapted to be cut by a scalpel blade. Alternatively, a very narrow slot can be substituted for the groove and thin membrane. At their free ends, the ribs 101 each have a V-shaped notch 103 centered with the respective groove 102 and forming with the groove a narrow throat area for laterally confining a scalpel blade. The box cover 67 has two retainer tabs 104 that are located to overlie respective ones of the rib grooves 102 when the cover is closed over the box 57. The base wall 80 is covered with a magnetic sheet 106 (FIG. 9) that includes a notch with portions that straddle along each side of the notch 98. The magnetic sheet 106 is mounted on the box wall with adhesive or other suitable means.

The four right angle tabs or legs 83 on the lower face of the base wall 80 are arranged in opposed pairs so that a longitudinal channel or receiving zone 109 is bounded by them and the base wall. A commercially available suture pack 110 comprising a plastic carrier supporting a needle and suture thread can be assembled into this receiving zone by pushing it between the tabs 83 and the lower surface of the base wall 80 from a loading zone formed by the lower face of the container box bottom wall 59 forward of the rear feet 66. A molded projection 115 (FIG. 8) stops the suture pack at an appropriate location. The right angle tabs or feet 83 are spaced from the plane of the base wall 80 so that they are resiliently flexed when the pack 110 is inserted and the pack is thereby reliably frictionally retained in position.

Figure 12:
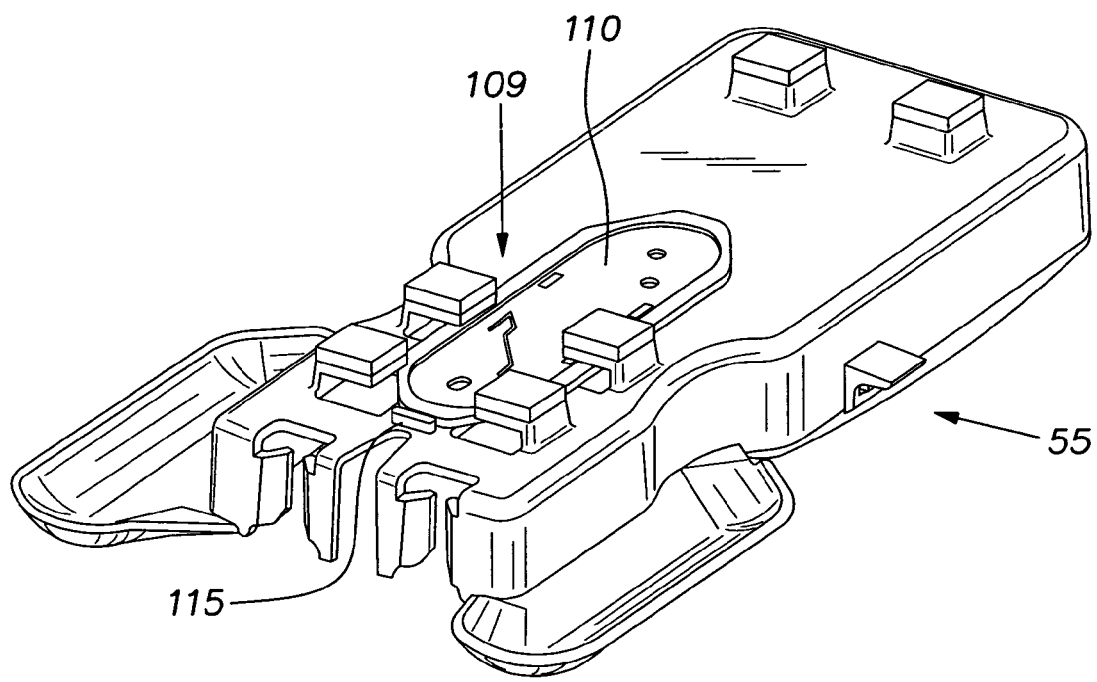
FIG. 12 is a perspective view of the bottom side of the device carrying a suture pack.

FIG. 12 illustrates a feature of the invention where the device 55 is used for presenting a suture needle 116 to a needle holder. As shown, the needle 116, which can be drawn from the suture pack 110, is positioned in straddled relation to the portion of the notch 98 in the base wall 80 and a complementary notch in the magnetic sheet 106. The needle 116 is held in the desired location by the magnetic attraction developed by the portions of the magnetic sheet 106 on opposite sides of the notch 98. The nose of a needle holder partially shown at 117 easily enters the area of the notch 98 and grips the mid-section of the needle 116. The needle 116 is then simply lifted off the magnetic sheet 116 for use.

FIG. 11 illustrates a manner of use of the device 55 that affords the least change in a surgeon's paradigm in being directly handed a scalpel by an attendant nurse and can therefore be highly preferably over other techniques and devices that avoid direct hand-to-hand exchange of scalpels. One or two scalpels 111 are mounted on the device 55 by forcing the scalpel blade 112 into a receiving zone of the membrane created by the groove 102 in an associated rib 101 and beneath the tabs 104 on the container cover 67. It will be understood that these elements along with the box end wall 61 confine or restrain the blade end of the scalpel 111 in essentially all directions except forward (away from the box end wall 61).

Figure 9:
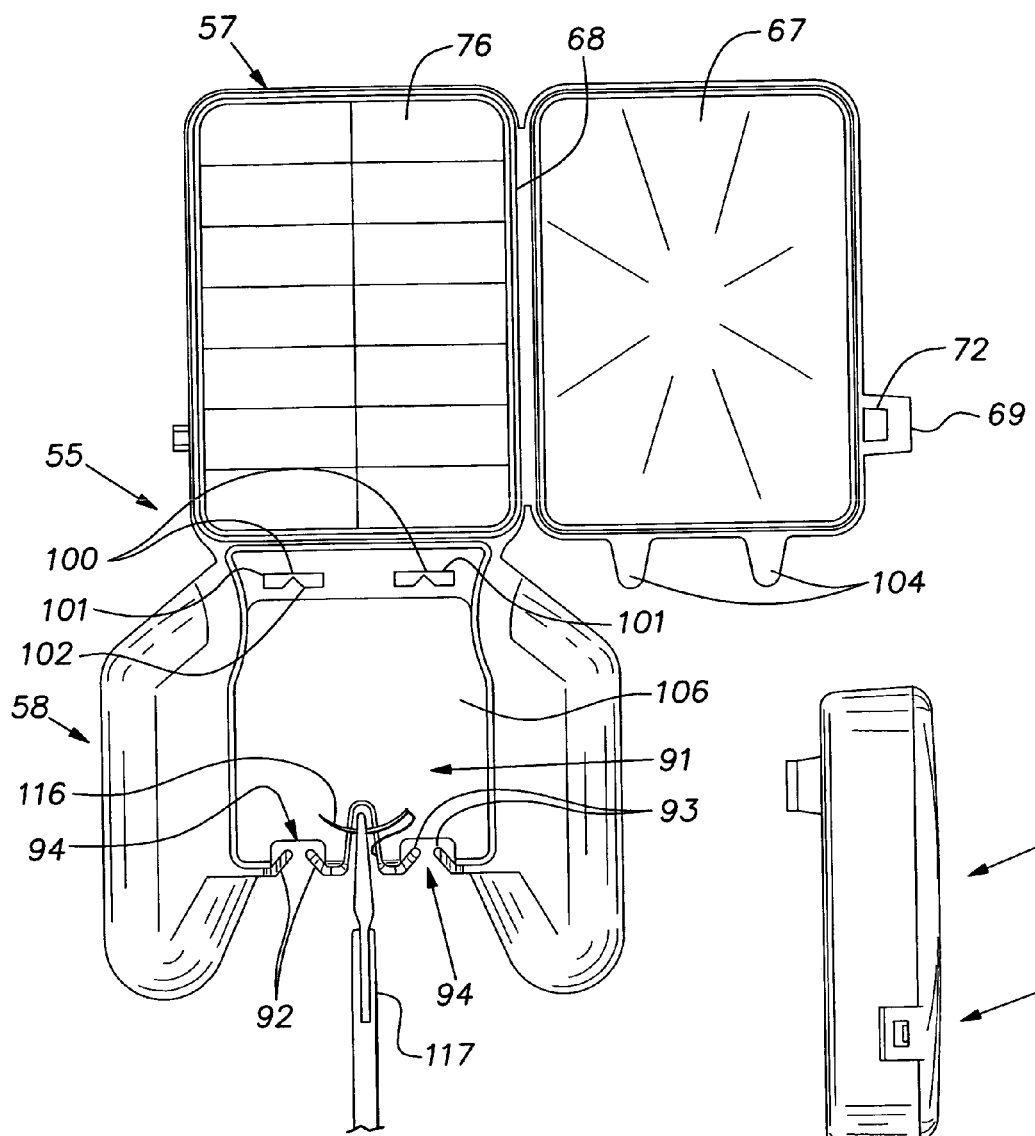
FIG. 9 is a plan view of the device of FIG. 7 shown with the cover open and with a magnetic sheet including a counting grid within a closable container portion of the body and a magnetic sheet on a forward or proximal end of the device.
Figure 10:
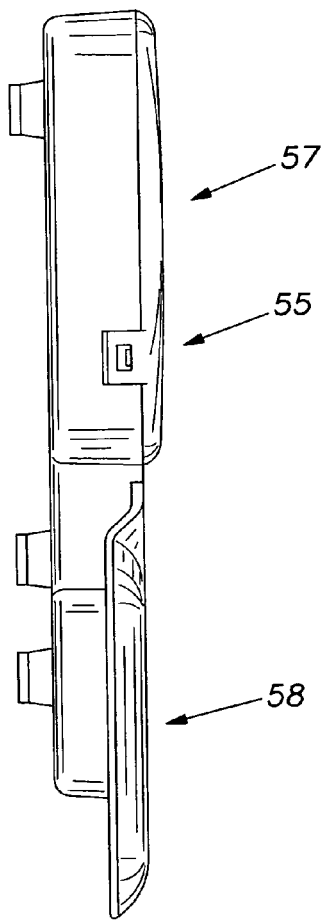
FIG. 10 is a side elevational view of the device of FIG. 7.

The convergent sides of the V-shaped notches 103 help to direct and center the scalpel blade 112 with the relevant blade rib 101 thereby facilitating action of the blade cutting into the membrane at the groove 102 or the alternative slot. During insertion of the scalpel blade 112 into the blade rib 101, the scalpel handle can be held above a respective gripping slot or gap 94. With the blade 112 set in the receiving zone formed by the rib 101, the scalpel handle, designated 113, is pushed down into the gap 94 in pitch motion preferably until it abuts the base wall 80 adjacent the gap. The convergent camming edges 97 at the gap 94 serve as cams to spread the tabs 92 to accommodate the particular width of the scalpel handle 113. A study of FIG. 9 shows that the vertical tabs 92 are oriented so that only their edges 93 engage the handle 113. The tab edges 93 are sharp enough to interengage with and grip typical serrations or ribs 114 on the scalpel handle 113. Because the tabs 92 are oblique to the longitudinal direction, they work like finger traps and prevent forward longitudinal movement of the scalpel, i.e. movement away from the container or box 57.

Because the grip of the tabs 92 is secure and reliable, the device 55 can be held upright or nearly upright (FIG. 11) by an attending nurse for presentation to a surgeon during an operation without the risk of a scalpel accidentally slipping out of the device. The scalpel 111 is simply retrieved from the device by pulling the handle 113 upwardly or away from the plane of the base wall 80, in pitch motion, so that the handle slides out of the gap 94 in a direction perpendicular to the base wall. It will be understood that the device 55 can alternatively be supported horizontally by a nurse or a support surface, and the scalpel 111 will be safely and securely held with the handle in cantilever relation to the support section 58 with its mid-section resting on the base wall 80.

The device 55 is ergonomically configured so that it can be securely gripped by the fingers of the nurse such as in the situation depicted in FIG. 11. The exterior of the walls 81, and, if desired, most or all of the remaining exterior of the body 56, except the cover 67, is formed with a non-slip surface by suitable surface treatment of the mold. Such body surfaces, preferably, have as a minimum surface roughness that which is formed by a vapor hone mold surface. The wasp waist section afforded by the concave areas 86 provides a secure grip between the thumb and a finger or fingers. The downwardly cupped edges 89 of the finger guards 88 automatically enable the person holding the device to locate his or her fingers so that they remain behind the guards 88. The cupped area on the forward end of the flanges or guards 88 is especially effective in receiving and constraining the small finger or pinky. Note that the finger guards are similarly useful when originally placing or replacing a scalpel on the device. With a person's fingers protected by the guards, the risk of an accidental stick or cut is effectively eliminated.

While the invention has been shown and described with respect to particular embodiments thereof, this is for the purpose of illustration rather than limitation, and other variations and modifications of the specific embodiments herein shown and described will be apparent to those skilled in the art all within the intended spirit and scope of the invention. Accordingly, the patent is not to be limited in scope and effect to the specific embodiments herein shown and described nor in any other way that is inconsistent with the extent to which the progress in the art has been advanced by the invention.

What is claimed is:

1. A device for no-hands transfer of a scalpel comprising an injection-molded thermoplastic body including an implement support section, a scalpel blade receiver adjacent one end of the support section, a scalpel handle grip adjacent an end of the support section opposite said one end, the blade receiver being arranged to limit freedom of movement of a blade laterally while allowing pitch movement of a handle of a scalpel, the handle grip being arranged to receive a mid-section of the handle of a scalpel in a pitch movement towards the support section while its blade is received in the blade receiver, the device having the handle grip being arranged to resist longitudinal reverse movement of the scalpel blade out of the blade receiver and the grip and pitch movement out of the handle grip with a friction force sufficient to reliably hold a straight scalpel handle in a gripped position while the device is handled by a surgical nurse to present the straight scalpel handle in a vertical or near vertical position for grasping by a surgeon with a large portion of the straight scalpel handle on a side of the handle grip remote from the blade receiver in a cantilever condition extending beyond said device such that it is free of physical interference from adjacent parts of the device, the body including opposed finger-grip areas spaced from one another by a width of the support section to enable the nurse to grasp the device, and laterally extending finger guards on opposite sides of the support section and laterally outward of said finger grip areas.

2. A device as set forth in claim 1, wherein the finger guards extend in a plane above a location to be occupied by a scalpel in the blade receiver and in the grip.

3. A device as set forth in claim 2, wherein the finger guards have laterally outward portions remote from said finger grip areas that extend downward from said plane.

4. A device as set forth in claim 1, wherein the finger grip areas have a wasp waist configuration that has a narrow zone between wider zones to facilitate fingertip grasping of the device.

5. A device as set forth in claim 1, wherein the blade receiver includes a narrow throat area to laterally confine the scalpel blade.

6. A device as set forth in claim 1, including a restraining portion that prevents a scalpel blade from being released in an upward direction.

7. A multi-purpose surgical sharps handling device comprising an injection-molded thermoplastic body including a scalpel holder and a closable sharps receiving container, the scalpel holder having a blade receiving zone and a handle gripping area that cooperate to support a scalpel with a straight handle in a cantilever arrangement whereby a substantial portion of the length of the straight scalpel handle is free of obstruction by the device in a space surrounding said substantial portion and it is thereby readily grasped, the receiving container being adjacent said blade receiving zone and remote from said handle gripping area, and finger grip areas and finger guards spaced on opposite sides of said scalpel holder arranged to protect the fingers of a nurse when holding the device at the spaced finger grip areas on opposite sides of a space between the blade receiving zone and the handle gripping area for presentation of the scalpel to a surgeon.

8. A surgical sharps handling device as set forth in claim 7, wherein said receiving container has a hinged cover and a releasable latch to maintain said cover closed on said container.

9. A surgical sharps handling device as set forth in claim 7, wherein said scalpel holder has a wasp waist area with a narrow zone between wider zones to obtain with one hand a positive finger hold of the device.

10. A surgical sharps handling device as set forth in claim 7, wherein the scalpel holder and sharps receiving container are accessible from a common face of the device.

11. A surgical sharps handling device as set forth in claim 10, including a suture pack mounting zone on a face of said device opposite said common face.

12. A device as set forth in claim 5, including a V-shaped notch for receiving and guiding the scalpel blade.

13. A device as set forth in claim 7, wherein a portion of said body has an exterior non-slip surface.

* * * * *